(12) United States Patent
Singh et al.

(10) Patent No.: US 10,331,850 B2
(45) Date of Patent: Jun. 25, 2019

(54) ESTIMATING BODY SURFACE MODELS OF PATIENTS

(71) Applicant: Siemens Healthcare GmbH, Erlangen (DE)

(72) Inventors: Vivek Kumar Singh, Monmouth Junction, NJ (US); Yao-jen Chang, Princeton, NJ (US); Kai Ma, Plainsboro, NJ (US); Terrence Chen, Princeton, NJ (US); Michael Wels, Bamberg (DE); Grzegorz Soza, Heroldsberg (DE)

(73) Assignee: Siemens Healthcare GmbH, Erlangen (DE)

( * ) Notice: Subject to any disclaimer, the term of this patent is extended or adjusted under 35 U.S.C. 154(b) by 933 days.

(21) Appl. No.: 14/606,745

(22) Filed: Jan. 27, 2015

(65) Prior Publication Data
US 2016/0306924 A1 Oct. 20, 2016

Related U.S. Application Data

(60) Provisional application No. 61/932,447, filed on Jan. 28, 2014.

(51) Int. Cl.
*G06F 16/51* (2019.01)
*G06F 19/00* (2018.01)
*G06N 20/00* (2019.01)
*G16H 30/00* (2018.01)

(52) U.S. Cl.
CPC ............ *G06F 19/321* (2013.01); *G06F 16/51* (2019.01); *G06N 20/00* (2019.01); *G16H 30/00* (2018.01)

(58) Field of Classification Search
CPC ...................................................... G16H 30/00
See application file for complete search history.

(56) References Cited

U.S. PATENT DOCUMENTS

| 2003/0176780 A1* | 9/2003 | Arnold ................. G06T 7/0012 600/407 |
| 2005/0048456 A1* | 3/2005 | Chefd'hotel .............. G06T 7/33 434/267 |
| 2009/0262886 A1* | 10/2009 | Mollus ................. A61B 6/4441 378/19 |

(Continued)

OTHER PUBLICATIONS

Y. Zheng, et al., "Four-Chamber Heart Modeling and Automatic Segmentation for 3D Cardiac CT Volumes Using Marginal Space Learning and Steerable Features," IEEE Transactions on Medical Imaging, vol. 27, Issue 11, pp. 1668-1681, 2008.

(Continued)

*Primary Examiner* — Sheetal R Paulson

(57) ABSTRACT

A method for estimating a body surface model of a patient includes: (a) segmenting, by a computer processor, three-dimensional sensor image data to isolate patient data from environmental data; (b) categorizing, by the computer processor, a body pose of the patient from the patient data using a first trained classifier; (c) parsing, by the computer processor, the patient data to an anatomical feature of the patient using a second trained classifier, wherein the parsing is based on a result of the categorizing; and (d) estimating, by the computer processor, the body surface model of the patient based on a result of the parsing. Systems for estimating a body surface model of a patient are described.

22 Claims, 8 Drawing Sheets

(56) References Cited

U.S. PATENT DOCUMENTS

| | | | | |
|---|---|---|---|---|
| 2009/0285357 | A1* | 11/2009 | Khamene | A61B 6/08 378/20 |
| 2011/0300929 | A1* | 12/2011 | Tardif | A63F 13/213 463/30 |
| 2012/0207359 | A1* | 8/2012 | Konukoglu | G06K 9/6277 382/128 |
| 2016/0109545 | A1* | 4/2016 | Forthmann | G01R 33/543 382/131 |

OTHER PUBLICATIONS

S. Bauer, et al., "Multi-modal Surface Registration for Markerless Initial Patient Setup in Radiation Therapy Using Microsoft's Kinect Sensor," IEEE International Conference on Computer Vision Workshops (ICCV Workshops), pp. 1175-1181, 2011.

* cited by examiner

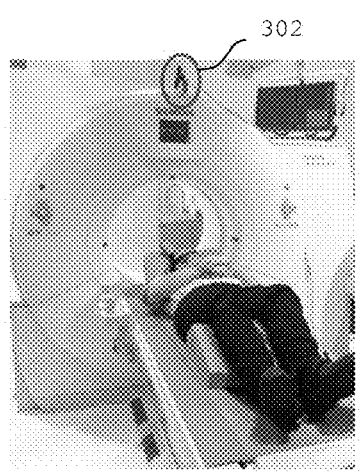
FIG. 3A
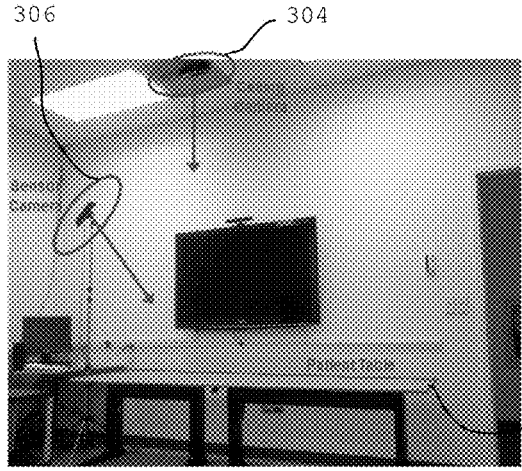
FIG. 3B
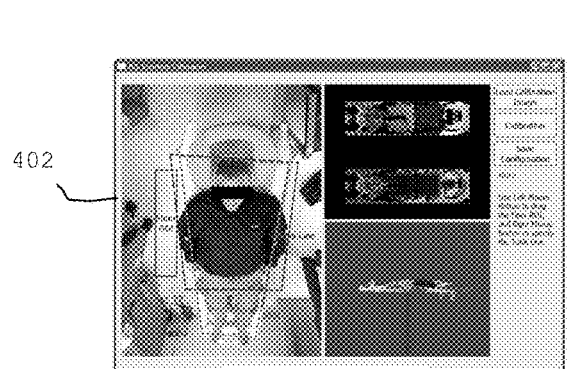
FIG. 4A
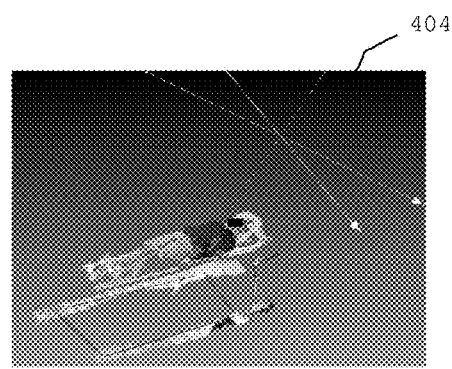
FIG. 4B
FIG. 5
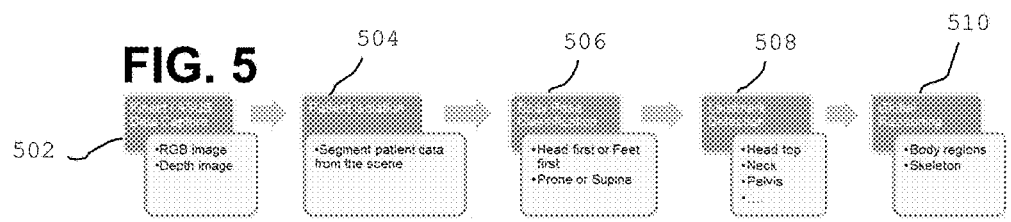

11002

ESTIMATING BODY SURFACE MODELS OF PATIENTS

RELATED APPLICATIONS

This application claims the benefit of U.S. Provisional Application No. 61/932,447, filed Jan. 28, 2014. The entire contents of the provisional application are incorporated herein by reference, except that in the event of any inconsistent disclosure or definition from the present specification, the disclosure or definition herein shall be deemed to prevail.

TECHNICAL FIELD

The present teachings relate generally to the estimation of patient body surface models from three-dimensional data.

BACKGROUND

Medical imaging refers to a variety of different techniques that may be used to create visual representations of interior regions of a patient's body. Medical imaging techniques—including but not limited to computed tomography (CT), magnetic resonance (MR), positron emission tomography (PET), single photon emission computed tomography (SPECT) data, and the like—may be used to reveal internal structures that would otherwise be concealed by a patient's skin and/or bones, and to diagnose and/or treat disease.

As a result of the extreme variation that may occur in patient body shapes, body sizes, clothing, and the like, a technician operating a medical imaging scanner may be faced with the difficult task of trying to determine, roughly, the hidden location of an internal organ or region of interest in a patient, and then manually positioning the patient such that the region of interest is optimally positioned with respect to the scanner. The manual patient positioning process is time-consuming and costly.

One approach suggested by Sebastian Bauer et al. to improve the manual patient positioning process in radiation therapy has been to use motion-sensing input devices (e.g., Microsoft Kinect) for coarse initial patient setup verification and alignment. However, this approach involves aligning the patient on a table based on a previously obtained CT scan in the diagnostic phase. Thus, a prior medical imaging scan (e.g., which may have already necessitated some degree of manual patient positioning) is a prerequisite to this approach.

SUMMARY

The scope of the present invention is defined solely by the appended claims, and is not affected to any degree by the statements within this summary.

In accordance with the present teachings, an approach for estimating the body surface model of a patient from data captured from a three-dimensional camera in a clinical setting (e.g., a CT scanning room) is described. The estimated model includes a three-dimensional surface reconstruction (e.g., point cloud or photo mesh), location of anatomical landmarks (e.g., neck, shoulders, groin, knee, etc.), as well as the extent of body regions (e.g., pelvis, abdomen, etc.). The landmarks and body regions provide an estimate of the expected internal organ positions. The model is estimated within the coordinate frame of the medical imaging scanner (e.g., CT scanner), and may be used in a variety of applications (e.g., including but not limited to automating the patient positioning process, which is currently done manually and is expensive).

By way of introduction, a computer-implemented method for estimating a body surface model of a patient in accordance with the present teachings includes: (a) segmenting, by a computer processor, three-dimensional sensor image data to isolate patient data from environmental data; (b) categorizing, by the computer processor, a body pose of the patient from the patient data using a first trained classifier; (c) parsing, by the computer processor, the patient data to an anatomical feature of the patient using a second trained classifier, wherein the parsing is based on a result of the categorizing; and (d) estimating, by the computer processor, the body surface model of the patient based on a result of the parsing.

A system for estimating a body surface model of a patient in accordance with the present teachings includes: (a) a processor; (b) a non-transitory memory coupled to the processor; (c) first logic stored in the memory and executable by the processor to cause the processor to segment three-dimensional sensor image data to isolate patient data from environmental data; (d) second logic stored in the non-transitory memory and executable by the processor to cause the processor to categorize a body pose of the patient from the patient data using a first trained classifier; (e) third logic stored in the non-transitory memory and executable by the processor to cause the processor to parse the patient data to identify an anatomical feature of the patient using a second trained classifier based on a category of the body pose; and (f) fourth logic stored in the non-transitory memory and executable by the processor to cause the processor to estimate the body surface model of the patient based on a parsing result.

A non-transitory computer readable storage medium in accordance with the present teachings has stored therein data representing instructions executable by a programmed processor for estimating a body surface model of a patient. The storage medium includes instructions for: (a) segmenting three-dimensional sensor image data to isolate patient data from environmental data; (b) categorizing a body pose of the patient from the patient data using a first trained classifier; (c) parsing the patient data to identify an anatomical feature of the patient using a second trained classifier, wherein the parsing is based on a result of the categorizing; and (d) estimating the body surface model of the patient based on a result of the parsing.

BRIEF DESCRIPTION OF THE DRAWINGS

FIGS. 3A and 3B show examples of empirically determined sensor placements.

FIGS. 4A and 4B show, respectively, a screenshot of an exemplary calibration tool and an example of a reconstructed scene based on estimated camera parameters.

FIG. 5 shows a schematic illustration of exemplary modules for an algorithm in accordance with the present teachings.

DETAILED DESCRIPTION

Methods and systems for estimating a body surface model of a patient in a clinical setup of a medical scanning room have been discovered and are described herein. The patient body surface model includes anatomical landmarks as well as the extent of body regions and may be used in a variety of applications. An overview of a representative algorithm for implementing a method in accordance with the present teachings—together with examples of representative applications of the algorithm—is shown in FIG. 1.

Figure 1:
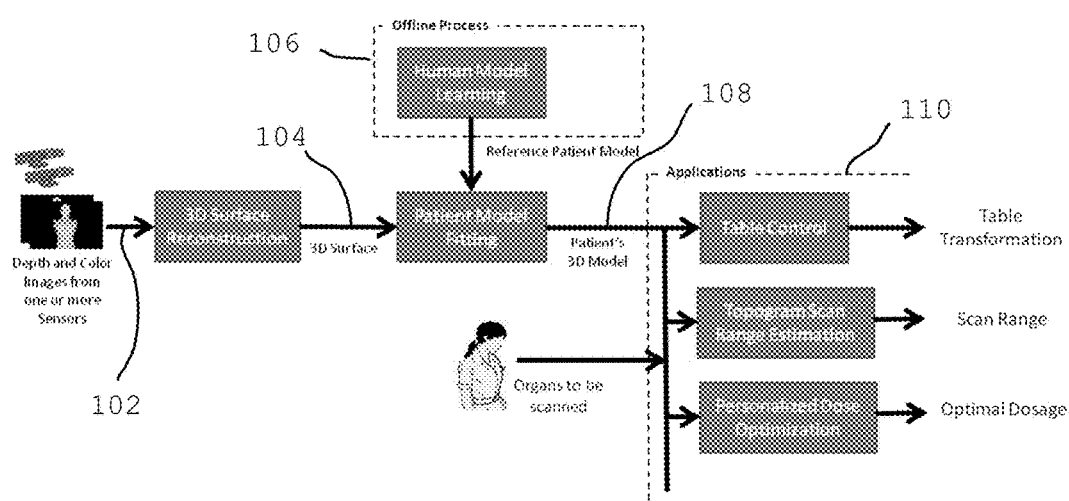
FIG. 1 shows a schematic overview of an exemplary algorithm in accordance with the present teachings, and various applications of the exemplary algorithm.

By way of introduction, as shown in FIG. 1, three-dimensional sensor image data—for example, depth information and, optionally, color image data obtained in a clinical setting (e.g., via a camera that provides depth information)—may be used as an input 102 in a three-dimensional surface reconstruction to provide a three-dimensional surface 104 of the patient (e.g., a point cloud, mesh, and/or the like). The three-dimensional surface 104—together with information provided in an offline process 106 (e.g., a statistical shaped model for the patient) may be used to develop a three-dimensional body surface model 108 of the patient. The body surface model 108 may be used in a variety of applications 110 as further described below. By way of example, as shown in FIG. 1, these applications include but are not limited to patient table transformations, topogram scan range estimations, personalized dose optimizations, and the like, and combinations thereof.

It is to be understood that elements and features of the various representative embodiments described below may be combined in different ways to produce new embodiments that likewise fall within the scope of the present teachings.

Figure 2:
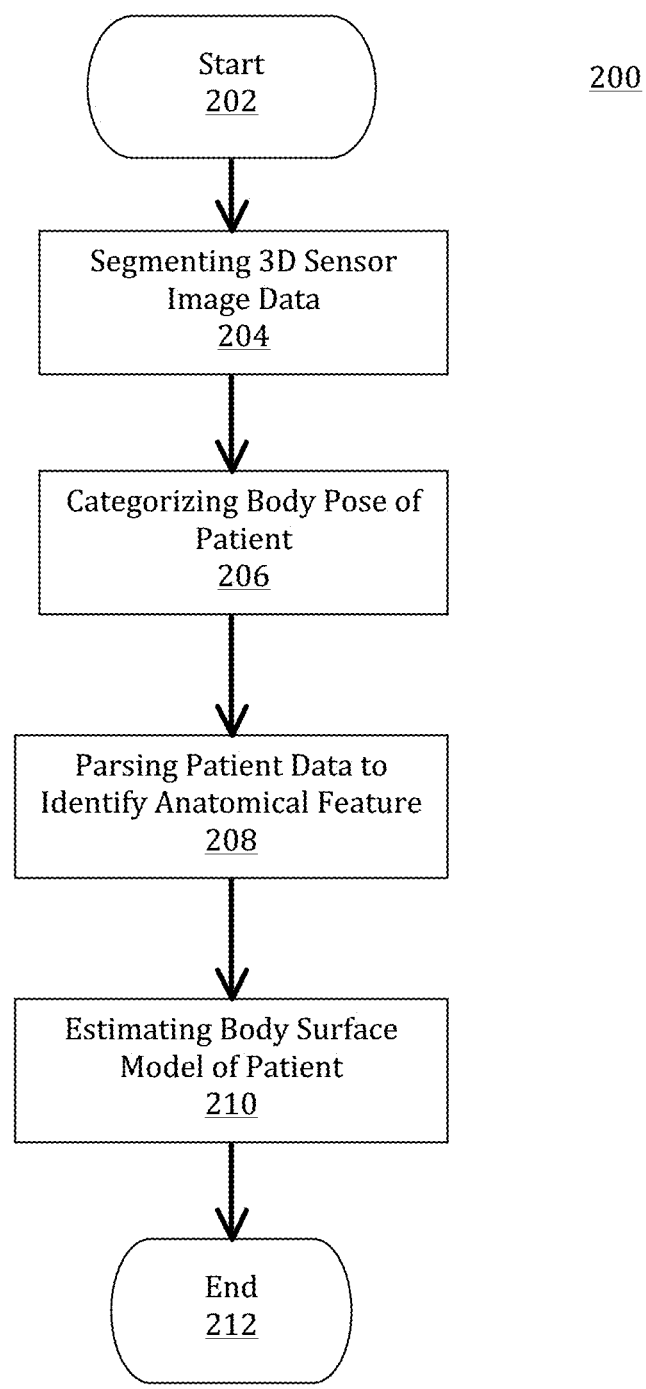
FIG. 2 shows a flow chart of a representative method for estimating a body surface model of a patient in accordance with the present teachings.

By way of general introduction, as shown in FIG. 2, an exemplary method 200 for estimating a body surface model of a patient in accordance with the present teachings begins at block 202 and includes: (a) segmenting 204 three-dimensional sensor image data to isolate patient data from environmental data; (b) categorizing 206 a body pose of the patient from the patient data using a first trained classifier; (c) parsing 208 the patient data to an anatomical feature of the patient using a second trained classifier, wherein the parsing is based on a result of the categorizing; and (d) estimating 210 the body surface model of the patient based on a result of the parsing. The method 200 ends at block 212.

It is to be understood that the relative ordering of some acts shown in the exemplary flow chart of FIG. 2 is meant to be merely representative rather than limiting, and that alternative sequences may be followed. Moreover, it is likewise to be understood that additional, different, or fewer acts may be provided. Moreover, in alternative embodiments, these acts may occur in a different sequential order and/or one or more of these acts may occur substantially contemporaneously.

In some embodiments, a method for estimating a body surface model of a patient in accordance with the present teachings further includes one or more of the following additional acts: (e) obtaining the three-dimensional sensor image data in a clinical setting; (f) planning an imaging scan of the patient based on the estimated body surface model; (g) automating the imaging scan based on a detected occupancy of a patient table; (h) adjusting a setting of a patient table based on the estimated body surface model; (i) optimizing a therapeutic dose provided to the patient based on the estimated body surface model (e.g., by using the body surface model to estimate the amount of fat on the patient's body); (j) determining a topogram scan range based on the estimated body surface model; and/or (k) outputting a depiction of the estimated body surface model via a graphical user interface.

In some embodiments, a method for estimating a body surface model of a patient in accordance with the present teachings is implemented using a computer and, in some embodiments, one or a plurality of the acts of (a) segmenting, (b) categorizing, (c) parsing, (d) estimating, (e) obtaining, (f) planning, (g) automating, (h) adjusting, (i) optimizing, (j) determining, and/or (k) outputting described above are performed by one or a plurality of processors. The processors are able to render more quickly and consistently than a person. For time constrained medical environment, processor-based image generation assists diagnosis and/or treatment in ways that a human created image could not.

In some embodiments, the three-dimensional sensor image data includes depth information data. In some embodiments, the depth information data are captured via a camera. An algorithm in accordance with the present teachings may be used with any type of camera that provides access to depth information regardless of the type of technology used to compute the depth information. Thus, all manner of depth cameras are contemplated for use in accordance with the present teachings, including but not limited to structured-light devices (e.g., Microsoft Kinect, ASUS Xtion), time-of-flight devices (e.g., Creative TOF cameras), and combinations thereof. In some embodiments, the three-dimensional sensor image data further includes color image data (e.g., an RGB image).

The placement of one or more cameras in the medical image scanning room (e.g., a CT scanning room, a PET scanning room, a MR scanning room, and/or the like) may be determined empirically in order to achieve optimal performance of the analytics. Various factors that may impact performance include, for example, the ease and/or expense of sensor installation, patient visibility constraints (e.g., the quality of the obtainable data), and sensor noise characteristics. Moreover, as further described below, there may be a trade-off between one or more of these factors. For example, with structured-light devices and time-of-flight devices, noise tends to increase as distance from the sensor increases. Moreover, depending on wavelength, noise may also increase in close proximity to the sensor. Thus, sensor noise characteristics may be balanced against the field of view of the sensor when determining placement of a sensor in accordance with the present teachings. If a sensor is positioned too far away from the patient, there may be too much noise. If a sensor is positioned too close to the patient, the field of view may be too narrow and the entirety of the patient may not be visible.

In accordance with the present teachings, the 3D point cloud of the patient may be reconstructed and used for further processing. To achieve reliable surface reconstruction from depth images, the cameras may be mounted such that the cameras have an unobstructed view of the patient lying on the patient table. Depending on the sensor noise characteristics (e.g., image quality, resolution of captured depth-image), the camera(s) may be mounted close to the scanner table while still being able to keep the entire patient within the camera view. FIG. 3 shows examples of representative sensor placements that have been determined empirically. In FIG. 3A, the camera 302 is positioned on the gantry of a CT scanner. In FIG. 3B, a first camera 304 is positioned on the ceiling directly above a patient table 308, and a second camera 306 is positioned at one end of the patient table 308 at an angle similar to the configuration of gantry camera 302 in FIG. 3A. The two locations—overhead and angled—each have their advantages and disadvantages. For example, with an overhead camera, the analytics problem is more constrained and more accurate results may be obtained. However, the overhead camera presents challenges from an installation perspective since it is to be mounted on the ceiling. By contrast, the angled camera may have a lower installation overhead (e.g., the camera may even be attached to the gantry at the time of shipment). However, with the angled view, some patient data may be obscured, as further described below in reference to FIG. 9B.

While a system in accordance with the present teachings may be implemented with either of the two camera positions shown, for example, in FIG. 3B, data may also be captured from both cameras and fused in order to obtain a more accurate 3D point cloud. Since the two cameras are fixed, the cameras may be stereo calibrated (e.g., camera positions may be estimated relative to one another). Such a calibration may only be performed once, such as when the cameras are initially mounted on the scanner. Given the calibration information, the data from the two cameras may then be combined to obtain a denser point cloud representation of the scene.

Calibrating a visual sensor accurately may be a challenging and expensive task. However, in accordance with the present teachings, only a rough calibration of the sensor may be performed. Calibration involves estimating the intrinsic camera parameters (e.g., focal length, etc.) and extrinsic camera parameters (e.g., position and orientation of the camera in the coordinate frame of the medical imaging scanner). For the intrinsic calibration parameters, the data provided by the manufacture (e.g., Microsoft, ASUS) may be used. For extrinsic calibration, a user interface may be used to estimate the parameters (e.g., in a semi-supervised manner). For example, a technician may mark a region on a camera image indicating the floor and the scanner table. Using this information, the parameters may be estimated with sufficient accuracy. FIG. 4 shows an example of a screenshot 402 of a representative calibration tool, and a reconstructed scene 404 based on the estimated camera parameters.

In accordance with the present teachings, a body surface model of a patient may be estimated from data captured from one or more depth cameras. Since the patient is lying on a patient table (which may be integrated into the medical imaging scanner), constraints may be placed on the patient's body pose relative to the scanner and, therefore, the depth cameras (which are mounted at fixed positions relative to the scanner). Furthermore, medical imaging scanning (e.g., CT scanning) often restricts the patient to one of a discrete number of poses depending on the body region to be scanned. For example, if a head scan is to be performed, the body pose may call for the patient's head to be placed close to the gantry with the patient's arms either folded across the patient's belly or placed at the patient's side. While these constraints substantially reduce the search space for a body surface model, the problem remains challenging due to the requisite high degree of accuracy and the variations resulting from patient clothing, body shape, and sensor noise.

An algorithm in accordance with the present teachings may include the following representative modules as shown in FIG. 5: (a) Patient Isolation 504 (e.g., to extract patient data from the image); (b) Body Pose Classification 506 (e.g., to classify a patient's body pose as prone or supine and head-first or feet-first); (c) Landmark Detection 508 (e.g., to fit a kinematic model with body landmarks as part of a patient surface model estimation); and (d) Global Reasoning 510 (e.g., to determine body regions taking, for example, patient height into account).

As shown in FIG. 5, an initial data capture 502 provides an input for patient isolation module 504. The data capture 502 provides a depth image and, optionally, a color image. Although the color image may be advantageous (e.g., from a UI perspective), the color image may not be available and is not required for use of the algorithm.

The segmenting 204 of three-dimensional sensor image data shown in the flowchart of FIG. 2 may include patient isolation as further described below. For example, the patient data isolated from the three-dimensional sensor image data includes imaging data corresponding to at least a portion of the patient and, in some embodiments, to substantially all of the patient. The patient data may further include a comparatively small amount of additional extraneous or non-patient imaging data (e.g., environmental data representing at least a portion of the clinical setting, a technician, patient clothing, and/or the like). In some embodiments, the patient data isolated from the three-dimensional sensor image data includes a point cloud. In other embodiments, the patient data isolated from the three-dimensional sensor image data includes a mesh. A point cloud is less constrained than a mesh, and may be used as the input of an algorithm in accordance with the present teachings. Although not required, a mesh—if available—provides additional information and may likewise be used as an input.

Given a three-dimensional surface (e.g., represented either as a mesh or a point cloud), the region containing only the patient and the table may be localized as described below. The localization may be performed efficiently based on knowledge of the relative position of the camera with respect to the scanner (e.g., established during the calibration process), knowledge of the dimensions of the patient table, and the fact that the points or region corresponding to the table (with the patient) may be separate from the rest of the scene.

Figures 6A, 6B:
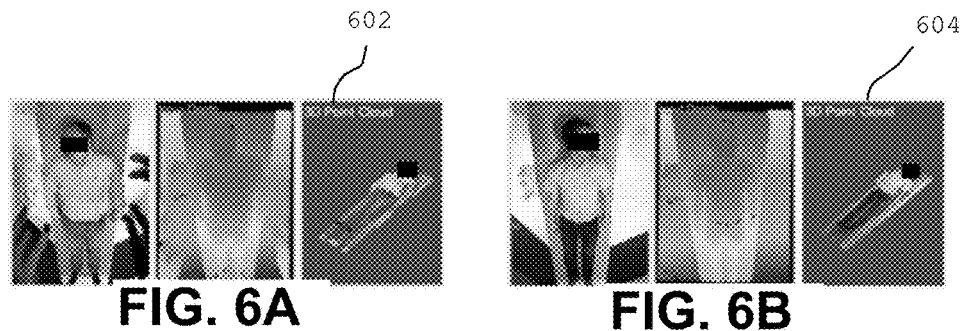
FIGS. 6A and 6B show examples of isolated patient point clouds.

As shown in FIG. 5, the three-dimensional sensor image data obtained in data capture 502 may serve as an input for the patient isolation module 504. The three-dimensional sensor image data may contain environmental data in addition to the desired patient data (e.g., part of the gantry, part of the floor, part of a nearby technician's body, etc.). Thus, in the patient isolation module 504, the region containing the entirety of the patient is extracted. Although the extraction may not be exact or precise, an effort is made to keep the extraction tight so that the amount of extraneous non-patient data carried over with the patient data is kept to a minimum. It may be difficult, for example to separate the patient table from the patient due to their close proximity. Thus, when the patient data is extracted, the table may come with the patient, as shown, for example, in the isolated patient point clouds 602 and 604 shown in FIGS. 6A and 6B, respectively. In some embodiments, the whole patient body is extracted and used as global information since having the context of the full body may prove advantageous. By contrast, if only a head region were extracted instead of a fully body, the head may be sized inaccurately since it lacks the global context of the body.

Once the patient data has been isolated via the patient module 504, a trained classifier may be used to classify the body pose of the patient in the body pose classification module 506. The body pose classification is a high level classification in which the patient may be classified into one or more body pose categories. In some embodiments the categorizing of the body pose includes classifying the body pose into a category selected from the group consisting of head-first, feet-first, prone (e.g., facing table), supine (e.g., facing ceiling), and combinations thereof. The body pose classification module 506 may use machine-learning technology.

For example, because the type of body poses and/or the space in which the body poses may be assumed are constrained, body pose may be estimated rapidly and with a high degree of accuracy. Given the patient data within the region of interest, classifiers may be applied to classify the patient pose as prone or supine, and as head-first or feet-first. In some embodiments, the Probabilistic Boosting Tree (PBT) may be used for this classification. The PBT is described, for example, in an article entitled "Four-chamber heart modeling and automatic segmentation for 3-D cardiac CT volumes using marginal space learning and steerable features" by: Yefeng Zheng, A. Barbu, B. Georgescu, M. Scheuering, and D. Comaniciu (*Medical Imaging, IEEE Transactions on*, 2008, 27, No. 11, 1668-1681). The entire contents of this document are hereby incorporated by reference, except that in the event of any inconsistent disclosure or definition from the present specification, the disclosure or definition herein shall be deemed to prevail.

For better results, the PBT framework may be extended to multiple channels by considering HAAR features extracted from grayscale image, depth image, and surface normal data. The consideration of multiple channels provides a substantial improvement over the use of only a single channel, such as a grayscale or depth image.

A head-first vs. feet-first classifier may be applied by considering only a part of the patient region of interest that is close to the sensor (e.g., the region covering the upper half of the body for a head-first case and the lower half of the body for a feet-first case). Depending upon whether the body pose is head-first or feet-first, a prone vs. supine classifier may then be applied. In some embodiments, separate prone classifiers are trained based on whether the patient is head-first or feet-first. The reason for training separate prone classifiers is that when the patient is lying on the patient table, the image statistics on the head in the head-first case are substantially different as compared to the feet-first case due to the distance from the sensor and the angle of the camera.

Once the body pose classification has been determined via the body pose classification module 506, a trained classier may be used to detect an anatomical feature of the patient. By way of example, the parsing 208 of patient data to identify an anatomical feature may include landmark detection and/or body region determination as further described below.

In some embodiments, the anatomical feature of the patient obtained via the parsing 208 includes a landmark (e.g., groin, left shoulder, right shoulder, left ankle, right ankle, left side of waist, right side of waist, left knee, right knee, and/or the like, and combinations thereof). Moreover, in some embodiments, the parsing includes enforcing one or a plurality of pairwise constraints between two or more of these landmarks. For example, given predefined landmarks of interest that are to be detected on a patient—together with knowledge of the body pose of the patient (e.g., head-first)—a machine-learning algorithm may be applied to detect the landmarks. Moreover, using knowledge that the distance between two landmarks (e.g., knee and ankle) for a patient of a given height is generally within a certain range, pairwise constraints between landmarks may be exploited to provide a good landmark model.

In some embodiments, the anatomical feature of the patient obtained via the parsing 208 includes a body region (e.g., head, torso, pelvis, upper legs, lower legs, and/or the like, and combinations thereof). Moreover, in some embodiments, the parsing includes enforcing one or a plurality of global constraints (e.g., height, weight, width, shape, and/or the like, and combinations thereof).

In some embodiments, the anatomical feature of the patient obtained via the parsing 208 includes a landmark and a body region and, in some embodiments, the parsing includes estimating a boundary of the body region based on a boundary estimate derived from the landmark.

Given the patient body pose and three-dimensional sensor image data, a sparse model fitting may be used to perform a coarse alignment of a patient surface model to the data. The fitting may be performed using a pictorial structure model of a patient lying on a table, whose parameters are obtained using an offline training process. The patient surface may be modeled using three body part regions (e.g., head, torso, and pelvis) and nine landmarks (e.g., groin, left and right shoulders, ankles, waist, and knees). For each of the body part regions and landmarks, a multi-channel PBT classifier may be trained that selects a best set of features from grayscale, depth, and surface normal images. Since the image statistics are substantially different, separate landmark detectors may be trained for data captured from a camera mounted on the gantry (e.g., with 45 degree tilt) and data captured from an overhead camera mounted on the ceiling.

For inference, the head and torso detectors may be applied, and a joint likelihood maximization may be performed to obtain the optimal head and torso estimates. Given these estimates, the pelvis classifier may be applied to obtain the best pelvis hypothesis. Given these body region estimates, the landmark detectors may be applied to localize the individual landmarks. This sequential process may have a lower accuracy as compared to a joint reasoning over all the body part regions and landmarks, but is substantially faster. Moreover, the accuracy of the obtained model may be sufficient to be further refined by subsequent modules.

Figures 7A, 7B, 7C, 7D:
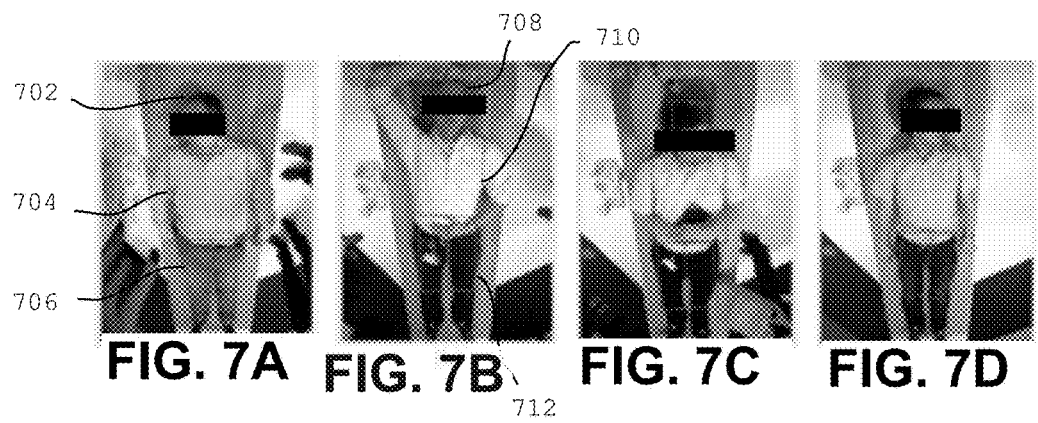
FIGS. 7A, 7B, 7C, and 7D show examples of body region detection results derived from data captured from a scanner/gantry camera.

FIG. 7 show examples of body part region detection using data captured from a scanner/gantry camera. For example, FIG. 7A shows a head region 702, a torso region 704, and an upper leg region 706. Similarly, FIG. 7B shows a head region 708, a torso region 710, and an upper leg region 712.

Once the landmarks have been detected via the landmark detection module 508 and a patient surface model with landmark positions and patient height is established, the extent of the various body regions (e.g., head, torso, pelvis, upper legs, and lower legs) may be determined. Although the detected landmarks already provide a boundary estimate for each body region, the landmark-based estimates may be slightly off due, for example, to the patient's clothing. Thus, to obtain a more accurate body region estimate, the region boundaries may be estimated by taking patient height into account. In the training phase, the distribution of the relative boundary position of the body regions with respect to patient height is learned. Given this distribution, the region boundary is simply constrained to lie within the feasible range and to be statistically close to the distribution.

Figures 8A, 8B, 8C:
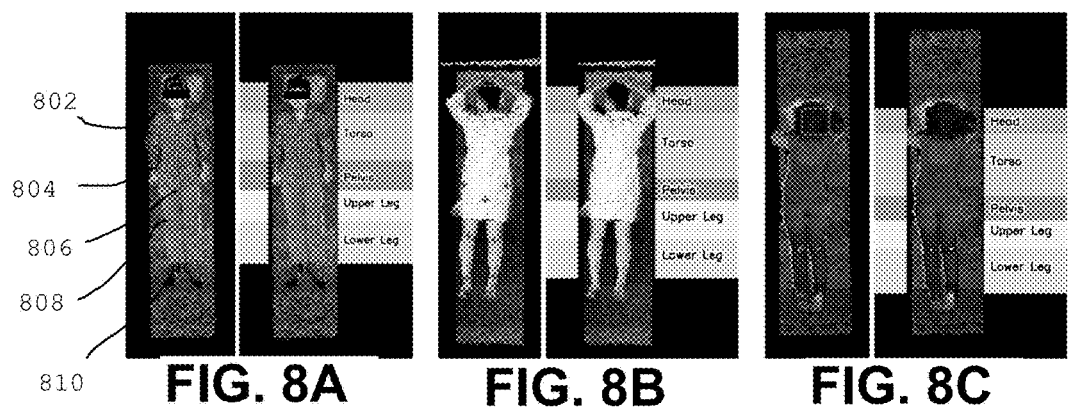
FIGS. 8A, 8B, and 8C show examples of landmark detection results derived from data captured from an overhead ceiling camera.

Landmark detection results on data captured from the ceiling camera and scanner/gantry camera are shown in FIGS. 8 and 9 respectively. As shown in FIG. 8A, several landmarks indicated by crosshair markings have been detected. These include the patient's right shoulder 802, right side of waist 804, groin 806, right knee 808, and right ankle 810. The landmarks shown in FIG. 8A have been predefined (prechosen) based on all of the potential body poses that may be adopted by the patient. These landmarks may also be used to estimate body part regions as shown, for example in the right-hand images in each of FIGS. 8A, 8B, and 8C, which depict approximate regions corresponding to the head, torso, pelvis, upper legs, and lower legs.

Figures 9A, 9B, 9C:
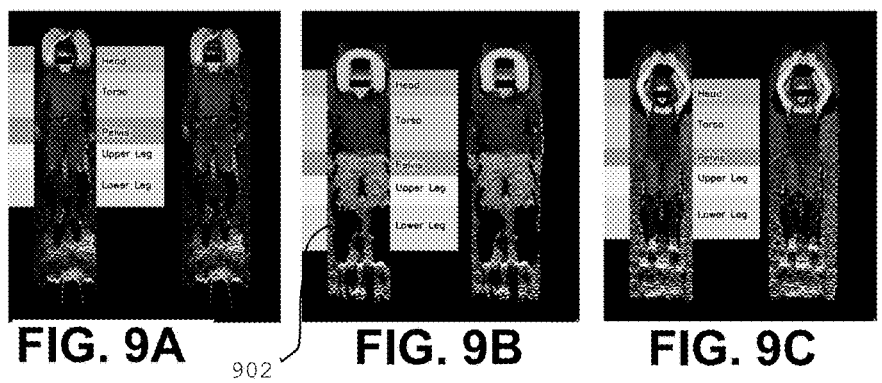
FIGS. 9A, 9B, and 9C show examples of landmark detection results derived from data captured from a scanner/gantry camera.

The landmark detection results on data captured from the angled scanner/gantry camera shown in FIG. 9 are illustrative of a potential disadvantage of using an angled camera as opposed to an overhead camera for data capture. For example, as shown in FIG. 9B, a region 902 below the patient's knees is entirely black because no corresponding data is available. Due to the placement of the sensor, the upper part of the patient's legs occluded the lower part. However, although the data have been obscured, the approximate location of the patient's feet may still be determined.

Figures 10A, 10B:
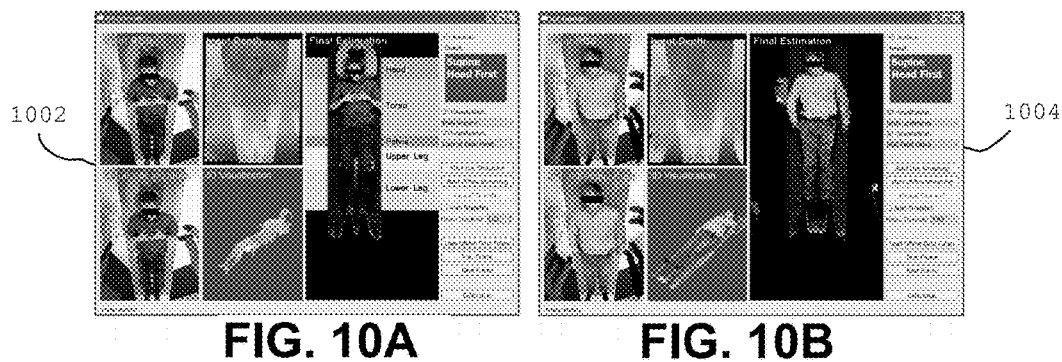
FIGS. 10A and 10B show examples of screenshots of a graphical user interface for use in accordance with the present teachings.

In some embodiments, a graphical user interface may be used to depict the results of a body surface model fitting in accordance with the present teachings, and to allow an operator to interact with and analyze the estimated patient surface model. By way of example, FIGS. 10A and 10B show representative screenshots 1002 and 1004, respectively, of a representative graphical user interface that may be used in accordance with the present teachings.

In some embodiments, the estimated body surface model obtained in accordance with the present teachings may be used in planning an imaging scan of a patient. All manner of imaging scans are contemplated for use in accordance with the present teachings, including but not limited to computed tomography (CT), magnetic resonance (MR), positron emission tomography (PET), single photon emission computed tomography (SPECT data), and/or the like, and combinations thereof.

In accordance with the present teachings, a prior medical imaging scan (e.g., a CT scan) is not required in order to align the patient for subsequent diagnostic testing. On the contrary, the present teachings may be applied in the diagnostic stage itself for planning and obtaining the initial medical imaging scan. The approach described herein provides a precise estimate of the patient surface model, while being fast enough for a seamless integration into the patient scanning workflow.

Figure 11A:
FIGS. 11A, 11B, and 11C show an example of an organ atlas superimposed on a patient's body.
Figure 11B:
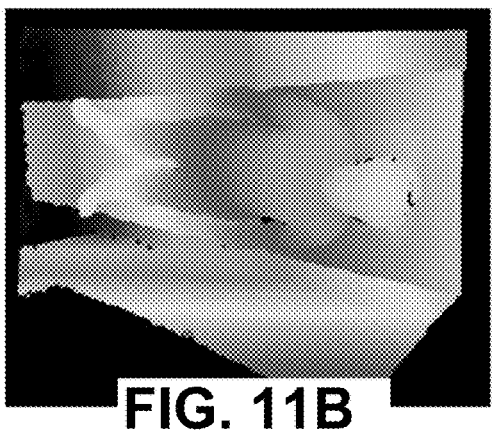
Figure 11C:
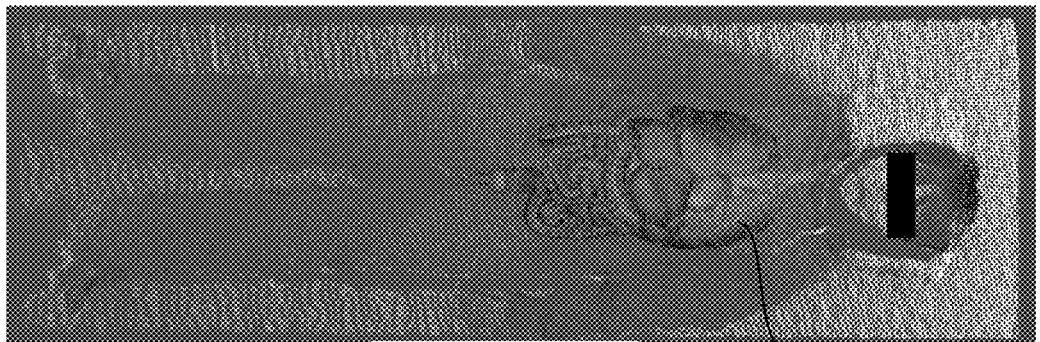

The present teachings may be applied in various ways, and the estimated body surface model may be used in a variety of ways. For example, in some embodiments, given the estimates of the body landmark positions, the approximate positions of a patient's internal organs may be predicted, and these positions may be visualized on the captured data (e.g., organ atlas visualization), thereby facilitating the specification of a scan range for a specific organ. FIG. 11 shows an example of an organ atlas 11002 superimposed on a patient's body.

In some embodiments, given the organ or the region of the body part to be scanned—together with the current position of the patient (and the table) obtained via model fitting—the transformation needed to move the table from its current position to an appropriate target position in the scanner (e.g., a precise table movement to the iso-center) may be estimated.

In some cases, the table movement itself may have a drift, and the final position of the table may not be close enough to the target position due to accumulation of position errors over time. In such cases, the model fitting may be performed multiple times, and the transformation to correct for the drift may be re-estimated.

In some embodiments, a system in accordance with the present teachings may continuously monitor the patient table, and the detection of a table occupancy may trigger an automatic scan. For example, once a patient is detected on the table, the system may automatically follow a procedure to fit the patient model and display the reconstructed model to an operator to specify the scan range and/or to select the organ to be scanned (e.g., from a drop down list on a graphical user interface). Once the scan range is determined, the medical imaging scan (e.g., CT scan) may be triggered. This automation may be efficiently integrated into the patient scanning workflow, since the operator may perform only one action to obtain the scan.

In some embodiments, as described above, the present teachings provide methods for estimating a body surface model of a patient. In other embodiments, as further described below, the present teachings also provide systems for estimating a body surface model of a patient.

Figure 12:
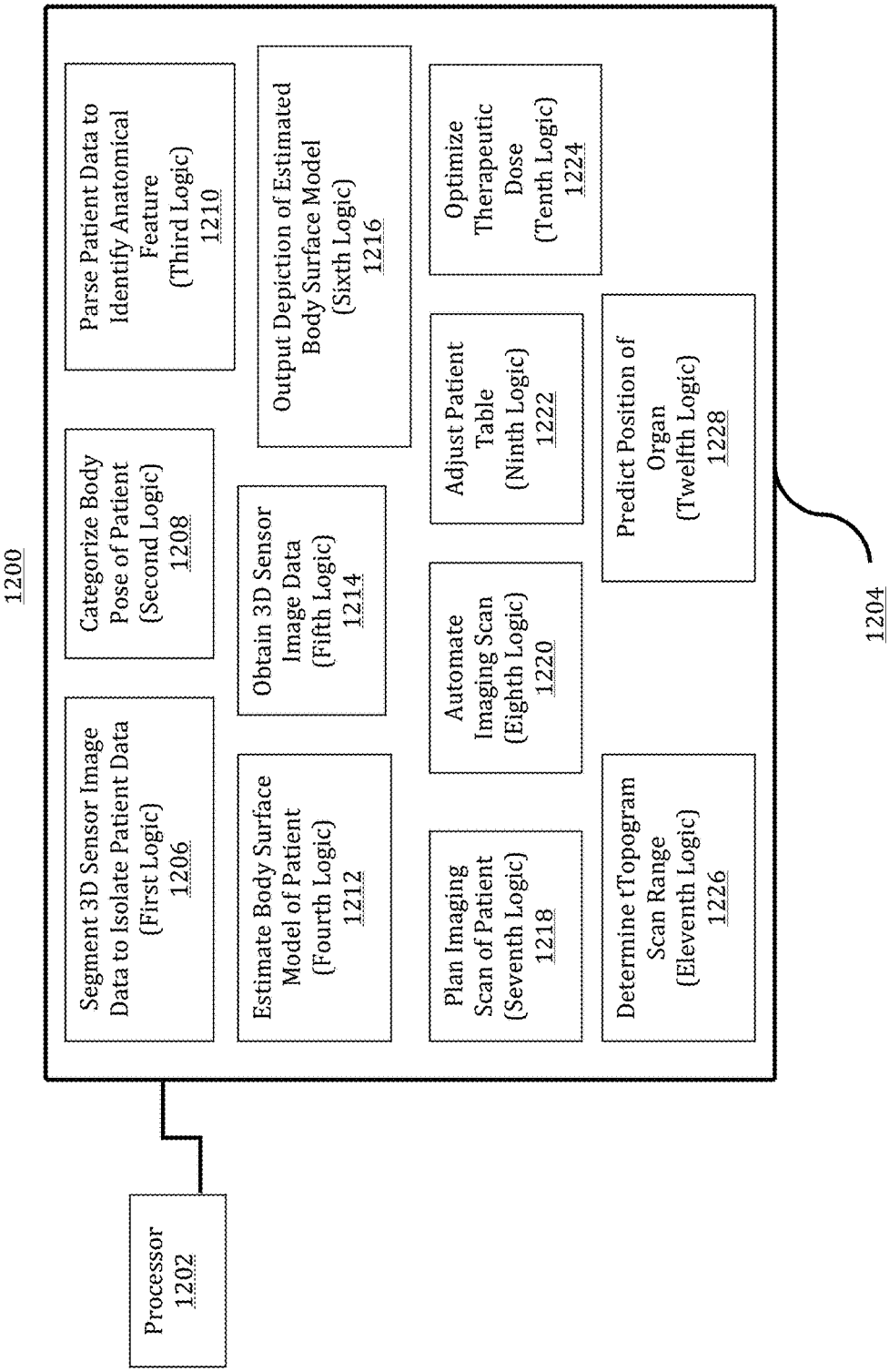
FIG. 12 shows a block diagram of a representative system for estimating a body surface model of a patient in accordance with the present teachings.

FIG. 12 shows a block diagram of a representative system 1200 for estimating a body surface model of a patient in accordance with the present teachings.

In some embodiments, as shown in FIG. 12, a system 1200 for estimating a body surface model of a patient in accordance with the present teachings is implemented as part of a body surface model estimation module in a computer system. As shown in FIG. 12, the system 1200 includes: a processor 1202; a non-transitory memory 1204 coupled with the processor 1202; first logic 1206 stored in the non-transitory memory 1204 and executable by the processor 1202 to cause the processor 1202 to segment three-dimensional sensor image data to isolate patient data from environmental data; second logic 1208 stored in the non-transitory memory 1204 and executable by the processor 1202 to cause the processor 1202 to categorize a body pose of the patient from the patient data using a first trained classifier; third logic 1210 stored in the non-transitory memory 1204 and executable by the processor 1202 to cause the processor 1202 to parse the patient data to identify an anatomical feature of the patient using a second trained classifier based on a category of the body pose; and fourth logic 1212 stored in the non-transitory memory 1204 and executable by the processor 1202 to cause the processor 1202 to estimate the body surface model of the patient based on a parsing result.

In some embodiments, the apparatus 1200 may further include one or more of the following: fifth logic 1214 stored in the non-transitory memory 1204 and executable by the processor 1202 to cause the apparatus 1200 to obtain the three-dimensional sensor image data in a clinical setting;

sixth logic 1216 stored in the non-transitory memory 1204 and executable by the processor 1202 to cause the apparatus 1200 to output a depiction of the estimated body surface model via a graphical user interface; seventh logic 1218 stored in the non-transitory memory 1204 and executable by the processor 1202 to cause the apparatus 1200 to plan an imaging scan of the patient based on the estimated body surface model; eighth logic 1220 stored in the non-transitory memory 1204 and executable by the processor 1202 to cause the apparatus 1200 to automate an imaging scan based on a detected occupancy of a patient table; ninth logic 1222 stored in the non-transitory memory 1204 and executable by the processor 1202 to cause the apparatus 1200 to adjust a setting of a patient table based on the estimated body surface model; tenth logic 1224 stored in the non-transitory memory 1204 and executable by the processor 1202 to cause the apparatus 1200 to optimize a therapeutic dose provided to the patient based on the estimated body surface model; eleventh logic 1226 stored in the non-transitory memory 1204 and executable by the processor 1202 to cause the apparatus 1200 to determine a topogram scan range based on the estimated body surface model; and/or twelfth logic 1228 stored in the non-transitory memory 1204 and executable by the processor 1202 to cause the apparatus 1200 to predict a position of an organ based on the estimated body surface model.

In some embodiments, the system 1200 may be coupled to other modules of a computer system and/or to databases so as to have access to relevant information as needed (e.g., human model learning, etc.) and initiate appropriate actions.

A non-transitory computer-readable storage medium in accordance with the present teachings has stored therein data representing instructions executable by a programmed processor for estimating a body surface model of a patient. The storage medium includes instructions for: (a) segmenting three-dimensional sensor image data to isolate patient data from environmental data; (b) categorizing a body pose of the patient from the patient data using a first trained classifier; (c) parsing the patient data to identify an anatomical feature of the patient using a second trained classifier, wherein the parsing is based on a result of the categorizing; and (d) estimating the body surface model of the patient based on a result of the parsing.

One or more modules or logic described herein may be implemented using, among other things, a tangible computer-readable medium comprising computer-executable instructions (e.g., executable software code). Alternatively, modules may be implemented as software code, firmware code, hardware, and/or a combination of the aforementioned. For example the modules may be embodied as part of a medical imaging scanner.

Figure 13:
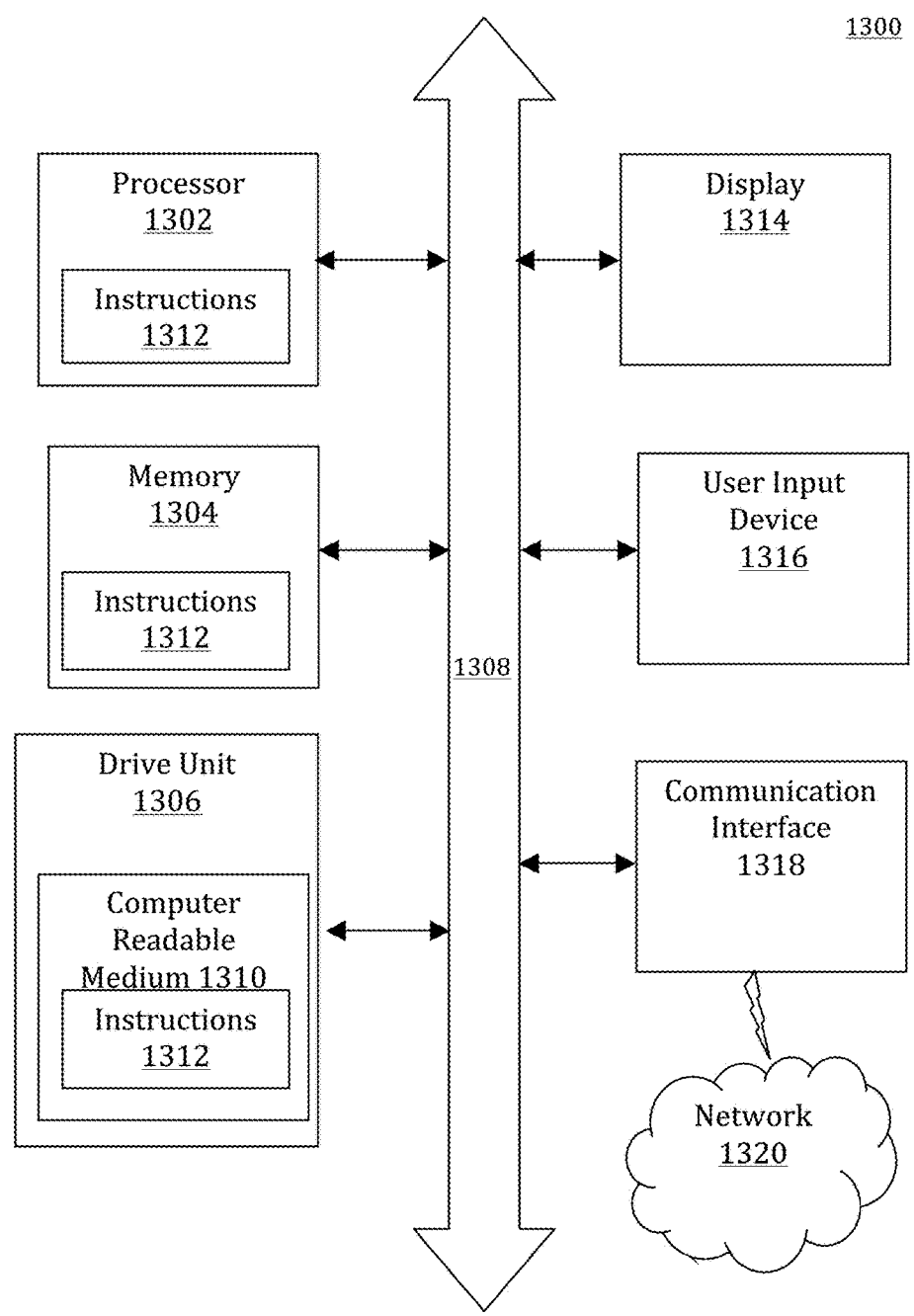
FIG. 13 shows a representative general computer system for use with a system in accordance with the present teachings.

FIG. 13 depicts an illustrative embodiment of a general computer system 1300. The computer system 1300 can include a set of instructions that can be executed to cause the computer system 1300 to perform any one or more of the methods or computer based functions disclosed herein. The computer system 1300 may operate as a standalone device or may be connected (e.g., using a network) to other computer systems or peripheral devices. Any of the components discussed above, such as the processor, may be a computer system 1300 or a component in the computer system 1300. The computer system 1300 may implement a medical imaging scanner, of which the disclosed embodiments are a component thereof.

In a networked deployment, the computer system 1300 may operate in the capacity of a server or as a client user computer in a client-server user network environment, or as a peer computer system in a peer-to-peer (or distributed) network environment. The computer system 1300 may also be implemented as or incorporated into various devices, such as a personal computer (PC), a tablet PC, a set-top box (STB), a personal digital assistant (PDA), a mobile device, a palmtop computer, a laptop computer, a desktop computer, a communications device, a wireless telephone, a land-line telephone, a control system, a camera, a scanner, a facsimile machine, a printer, a pager, a personal trusted device, a web appliance, a network router, switch or bridge, or any other machine capable of executing a set of instructions (sequential or otherwise) that specify actions to be taken by that machine. In some embodiments, the computer system 1300 may be implemented using electronic devices that provide voice, video or data communication. Further, while a single computer system 1300 is illustrated, the term "system" shall also be taken to include any collection of systems or sub-systems that individually or jointly execute a set, or multiple sets, of instructions to perform one or more computer functions.

As shown in FIG. 13, the computer system 1300 may include a processor 1302, for example a central processing unit (CPU), a graphics-processing unit (GPU), or both. The processor 1302 may be a component in a variety of systems. For example, the processor 1302 may be part of a standard personal computer or a workstation. The processor 1302 may be one or more general processors, digital signal processors, application specific integrated circuits, field programmable gate arrays, servers, networks, digital circuits, analog circuits, combinations thereof, or other now known or later developed devices for analyzing and processing data. The processor 1302 may implement a software program, such as code generated manually (i.e., programmed).

The computer system 1300 may include a memory 1304 that may communicate via a bus 1308. The memory 1304 may be a main memory, a static memory, or a dynamic memory. The memory 1304 may include, but is not limited to, computer-readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In some embodiments, the memory 1304 includes a cache or random access memory for the processor 1302. In alternative embodiments, the memory 1304 is separate from the processor 1302, such as a cache memory of a processor, the system memory, or other memory. The memory 1304 may be an external storage device or database for storing data. Examples include a hard drive, compact disc (CD), digital video disc (DVD), memory card, memory stick, floppy disc, universal serial bus (USB) memory device, or any other device operative to store data. The memory 1304 is operable to store instructions executable by the processor 1302. The functions, acts or tasks illustrated in the figures or described herein may be performed by the programmed processor 1302 executing the instructions 1312 stored in the memory 1304. The functions, acts or tasks are independent of the particular type of instructions set, storage media, processor or processing strategy and may be performed by software, hardware, integrated circuits, firm-ware, microcode and the like, operating alone or in combination. Likewise, processing strategies may include multiprocessing, multitasking, parallel processing and the like.

As shown in FIG. 13, the computer system 1300 may further include a display unit 1314, such as a liquid crystal display (LCD), an organic light emitting diode (OLED), a flat panel display, a solid state display, a cathode ray tube (CRT), a projector, a printer or other now known or later developed display device for outputting determined information. The display 1314 may act as an interface for the user to see the functioning of the processor 1302, or specifically as an interface with the software stored in the memory 1304 or in the drive unit 1306. A value or image based on the modeling may be output to the user on the display unit 1314. For example, an image representing at least a portion of the patient with modulation or alphanumeric text representing a calculated value may be indicated in the image.

Additionally, as shown in FIG. 13, the computer system 1300 may include an input device 1316 configured to allow a user to interact with any of the components of system 1300. The input device 1316 may be a number pad, a keyboard, or a cursor control device, such as a mouse, or a joystick, touch screen display, remote control or any other device operative to interact with the system 1300.

In some embodiments, as shown in FIG. 13, the computer system 1300 may also include a disk or optical drive unit 1306. The disk drive unit 1306 may include a computer-readable medium 1310 in which one or more sets of instructions 1312 (e.g., software) may be embedded. Further, the instructions 1312 may embody one or more of the methods or logic as described herein. In some embodiments, the instructions 1312 may reside completely, or at least partially, within the memory 1304 and/or within the processor 1302 during execution by the computer system 1300. The memory 1304 and the processor 1302 also may include computer-readable media as described above.

The present teachings contemplate a computer-readable medium that includes instructions 1312 or receives and executes instructions 1312 responsive to a propagated signal, so that a device connected to a network 1320 may communicate voice, video, audio, images or any other data over the network 1320. Further, the instructions 1312 may be transmitted or received over the network 1320 via a communication interface 1318. The communication interface 1318 may be a part of the processor 1302 or may be a separate component. The communication interface 1318 may be created in software or may be a physical connection in hardware. The communication interface 1318 is configured to connect with a network 1320, external media, the display 1314, or any other components in system 1300, or combinations thereof. The connection with the network 1320 may be a physical connection, such as a wired Ethernet connection or may be established wirelessly as discussed below. Likewise, the additional connections with other components of the system 1300 may be physical connections or may be established wirelessly.

The network 1320 may include wired networks, wireless networks, or combinations thereof. The wireless network may be a cellular telephone network, an 802.11, 802.16, 802.20, or WiMax network. Further, the network 1320 may be a public network, such as the Internet, a private network, such as an intranet, or combinations thereof, and may utilize a variety of networking protocols now available or later developed including, but not limited to TCP/IP based networking protocols.

Embodiments of the subject matter and the functional operations described in this specification may be implemented in digital electronic circuitry, or in computer software, firmware, or hardware, including the structures disclosed in this specification and their structural equivalents, or in combinations of one or more of them. Embodiments of subject matter described in this specification may be implemented as one or more computer program products, for example, one or more modules of computer program instructions encoded on a computer-readable medium for execution by, or to control the operation of, data processing apparatus. While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein. The computer-readable medium may be a machine-readable storage device, a machine-readable storage substrate, a memory device, or a combination of one or more of them. The term "data processing apparatus" encompasses all apparatuses, devices, and machines for processing data, including but not limited to, by way of example, a programmable processor, a computer, or multiple processors or computers. The apparatus may include, in addition to hardware, code that creates an execution environment for the computer program in question (e.g., code that constitutes processor firmware, a protocol stack, a database management system, an operating system, or a combination thereof).

In some embodiments, the computer-readable medium may include a solid-state memory such as a memory card or other package that houses one or more non-volatile read-only memories. Further, the computer-readable medium may be a random access memory or other volatile re-writable memory. Additionally, the computer-readable medium may include a magneto-optical or optical medium, such as a disk or tapes or other storage device to capture carrier wave signals such as a signal communicated over a transmission medium. A digital file attachment to an e-mail or other self-contained information archive or set of archives may be considered a distribution medium that is a tangible storage medium. Accordingly, the present teachings are considered to include any one or more of a computer-readable medium or a distribution medium and other equivalents and successor media, in which data or instructions may be stored.

In some embodiments, dedicated hardware implementations, such as application specific integrated circuits, programmable logic arrays and other hardware devices, may be constructed to implement one or more of the methods described herein. Applications that may include the apparatus and systems of various embodiments may broadly include a variety of electronic and computer systems. One or more embodiments described herein may implement functions using two or more specific interconnected hardware modules or devices with related control and data signals that may be communicated between and through the modules, or as portions of an application-specific integrated circuit. Accordingly, the present system encompasses software, firmware, and hardware implementations.

In some embodiments, the methods described herein may be implemented by software programs executable by a computer system. Further, in some embodiments, implementations may include distributed processing, component/object distributed processing, and parallel processing. Alternatively, virtual computer system processing may be constructed to implement one or more of the methods or functionality as described herein.

Although the present teachings describe components and functions that may be implemented in particular embodiments with reference to particular standards and protocols, the present invention is not limited to such standards and protocols. For example, standards for Internet and other packet switched network transmission (e.g., TCP/IP, UDP/IP, HTML, HTTP, HTTPS) represent examples of the state of the art. Such standards are periodically superseded by faster or more efficient equivalents having essentially the same functions. Accordingly, replacement standards and protocols having the same or similar functions as those disclosed herein are considered equivalents thereof.

A computer program (also known as a program, software, software application, script, or code) may be written in any form of programming language, including compiled or interpreted languages, and it may be deployed in any form, including as a standalone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described herein may be performed by one or more programmable processors executing one or more computer programs to perform functions by operating on input data and generating output. The processes and logic flows may also be performed by, and apparatus may also be implemented as, special purpose logic circuitry, for example, an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The main elements of a computer are a processor for performing instructions and one or more memory devices for storing instructions and data. Generally, a computer will also include, or be operatively coupled to receive data from or transfer data to, or both, one or more mass storage devices for storing data, for example, magnetic, magneto optical disks, or optical disks. However, a computer need not have such devices. Moreover, a computer may be embedded in another device, for example, a mobile telephone, a personal digital assistant (PDA), a mobile audio player, a Global Positioning System (GPS) receiver, to name just a few. Computer-readable media suitable for storing computer program instructions and data include all forms of non volatile memory, media and memory devices, including but not limited to, by way of example, semiconductor memory devices (e.g., EPROM, EEPROM, and flash memory devices); magnetic disks (e.g., internal hard disks or removable disks); magneto optical disks; and CD ROM and DVD-ROM disks. The processor and the memory may be supplemented by, or incorporated in, special purpose logic circuitry.

To provide for interaction with a user, some embodiments of subject matter described herein may be implemented on a device having a display, for example a CRT (cathode ray tube) or LCD (liquid crystal display) monitor, for displaying information to the user and a keyboard and a pointing device, for example a mouse or a trackball, by which the user may provide input to the computer. Other kinds of devices may be used to provide for interaction with a user as well. By way of example, feedback provided to the user may be any form of sensory feedback (e.g., visual feedback, auditory feedback, or tactile feedback); and input from the user may be received in any form, including but not limited to acoustic, speech, or tactile input.

Embodiments of subject matter described herein may be implemented in a computing system that includes a back-end component, for example, as a data server, or that includes a middleware component, for example, an application server, or that includes a front end component, for example, a client computer having a graphical user interface or a Web browser through which a user may interact with an implementation of the subject matter described in this specification, or any combination of one or more such back end, middleware, or front end components. The components of the system may be interconnected by any form or medium of digital data communication, for example, a communication network. Examples of communication networks include but are not limited to a local area network (LAN) and a wide area network (WAN), for example, the Internet.

The computing system may include clients and servers. A client and server are generally remote from each other and typically interact through a communication network. The relationship of client and server arises by virtue of computer programs running on the respective computers and having a client-server relationship to each other.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

While this specification contains many specifics, these should not be construed as limitations on the scope of the invention or of what may be claimed, but rather as descriptions of features specific to particular embodiments. Certain features that are described in this specification in the context of separate embodiments may also be implemented in combination in a single embodiment. Conversely, various features that are described in the context of a single embodiment may also be implemented in multiple embodiments separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings and described herein in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 CFR § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding claim—whether independent or dependent—and that such new combinations are to be understood as forming a part of the present specification.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

The invention claimed is:

1. A method for estimating a body surface model of a patient, the method comprising:
   acquiring, by at least one camera located at a camera position, three-dimensional sensor image data of an exterior of a patient;
   identifying, by a computer processor, an image scanner position of an image scanner and dimensions of a patient table;
   localizing, by the computer processor, the three-dimensional sensor image data as a function of the dimensions of the patient table and a relationship of the camera position and the image scanner position;
   segmenting, by a computer processor, the localized three-dimensional sensor image data;
   isolating, by the computer processor, patient data from environmental data in the segmented three-dimensional sensor image data;
   identifying, using a first trained classifier, a category of a body pose of the patient from the patient data;
   selecting, by the computer processor, a second trained classifier as a function of the category identified by the first trained classifier;
   parsing, by the second trained classifier, the patient data to an anatomical feature of the patient based on the category;
   estimating, by the computer processor, the body surface model of the patient based on a result of the parsing; and
   displaying the estimated body surface model for use in an imaging scan by the image scanner.

2. The method of claim 1 further comprising obtaining the three-dimensional sensor image data in a clinical setting.

3. The method of claim 1 wherein the three-dimensional sensor image data comprises depth information data.

4. The method of claim 3 wherein the depth information data is captured via a structured-light device, a time-of-flight device, or a combination thereof.

5. The method of claim 3 wherein the three-dimensional sensor image data further comprises an RGB image.

6. The method of claim 1 wherein the identifying the category comprises classifying the body pose into the category selected from the group consisting of head-first, feet-first, prone, supine, and combinations thereof.

7. The method of claim 1 wherein the anatomical feature comprises a landmark, and wherein the parsing comprises enforcing one or a plurality of pairwise constraints between a plurality of landmarks.

8. The method of claim 7 wherein the landmark is selected from the group consisting of groin, left shoulder, right shoulder, left ankle, right ankle, left side of waist, right side of waist, left knee, right knee, and combinations thereof.

9. The method of claim 8 wherein the anatomical feature further comprises a body region, and wherein the parsing comprises enforcing one or a plurality of global constraints.

10. The method of claim 9 wherein the body region is selected from the group consisting of head, torso, pelvis, upper legs, lower legs, and combinations thereof.

11. The method of claim 9 wherein the global constraints are selected from the group consisting of height, weight, width, shape, and combinations thereof.

12. The method of claim 1 wherein the anatomical feature comprises a landmark and a body region, and wherein the parsing comprises estimating a boundary of the body region based on a boundary estimate derived from the landmark.

13. The method of claim 1 wherein the imaging scan is selected from the group consisting of computed tomography (CT), magnetic resonance (MR), positron emission tomography (PET), single photon emission computed tomography (SPECT data), and combinations thereof.

14. The method of claim 13 further comprising automating the imaging scan based on a detected occupancy of a patient table.

15. The method of claim 1 further comprising adjusting a setting of a patient table based on the estimated body surface model.

16. The method of claim 1 further comprising determining a topogram scan range based on the estimated body surface model.

17. The method of claim 1 further comprising outputting a depiction of the estimated body surface model via a graphical user interface.

18. The method of claim 1 wherein the patient data isolated from the three-dimensional sensor image data comprises a point cloud.

19. The method of claim 1 wherein the patient data isolated from the three-dimensional sensor image data comprises a mesh.

20. A system for estimating a body surface model of a patient, the system comprising:
at least one camera positioned at a camera position, the at least one camera configured to acquire three-dimensional sensor image data;
a processor;
a non-transitory memory coupled with the processor;
first logic stored in the non-transitory memory and executable by the processor to cause the processor to localize the three-dimensional sensor image data as a function of dimensions of a patient table and a relationship of the camera position and an image scanner position;
second logic stored in the non-transitory memory and executable by the processor to cause the processor to segment the three-dimensional sensor image data into patient data and environmental data;
third logic stored in the non-transitory memory and executable by the processor to cause the processor to identify a category of a body pose of the patient from the patient data using a first trained classifier;
fourth logic stored in the non-transitory memory and executable by the processor to cause the processor to select a second trained classifier as a function of the category identified by the first trained classifier;
fifth logic stored in the non-transitory memory and executable by the processor to cause the processor to parse the patient data to identify an anatomical feature of the patient using a second trained classifier; and
sixth logic stored in the non-transitory memory and executable by the processor to cause the processor to estimate the body surface model of the patient based on a parsing result.

21. The system of claim 20 further comprising:
seventh logic stored in the non-transitory memory and executable by the processor to cause the processor to obtain the three-dimensional sensor image data in a clinical setting; and
eighth logic stored in the non-transitory memory and executable by the processor to cause the processor to output a depiction of the estimated body surface model via a graphical user interface.

22. A non-transitory computer-readable storage medium having stored therein data representing instructions executable by a programmed processor for estimating a body surface model of a patient, the storage medium comprising instructions for:
retrieving three-dimensional sensor image data from at least one camera positioned at a camera position;
localizing the three-dimensional sensor image data as a function of the camera position, an image scanner position, and dimensions of a patient table;
segmenting the localized three-dimensional sensor image;
isolating patient data from environmental data in the segmented three-dimensional sensor image data;
identifying, using a first trained classifier, a category of a body pose of the patient from the patient data;
selecting a second trained classifier as a function of the identified category;
parsing the patient data to identify an anatomical feature of the patient using the second trained classifier; and
estimating the body surface model of the patient based on a result of the parsing.

* * * * *